(12) United States Patent
Hudak, Jr.

(10) Patent No.: US 10,022,133 B2
(45) Date of Patent: Jul. 17, 2018

(54) SURGICAL TOOL WITH SHROUD AND ALIGNMENT FEATURE

(71) Applicant: Zimmer, Inc., Warsaw, IN (US)

(72) Inventor: John J. Hudak, Jr., Winona Lake, IN (US)

(73) Assignee: Zimmer, Inc., Warsaw, IN (US)

(*) Notice: Subject to any disclaimer, the term of this patent is extended or adjusted under 35 U.S.C. 154(b) by 293 days.

(21) Appl. No.: 14/868,697

(22) Filed: Sep. 29, 2015

(65) Prior Publication Data

US 2016/0143650 A1    May 26, 2016

Related U.S. Application Data

(60) Provisional application No. 62/082,249, filed on Nov. 20, 2014.

(51) Int. Cl.
   *A61B 17/16*    (2006.01)
   *A61B 17/17*    (2006.01)

(52) U.S. Cl.
   CPC ...... *A61B 17/1666* (2013.01); *A61B 17/1746* (2013.01)

(58) Field of Classification Search
   CPC .................. A61B 17/1671; A61B 17/1666
   See application file for complete search history.

(56) References Cited

U.S. PATENT DOCUMENTS

| | | | |
|---|---|---|---|
| 7,670,343 B2* | 3/2010 | Meridew | A61B 17/1666 606/81 |
| 7,722,613 B2* | 5/2010 | Sutterlin | A61B 17/0206 606/79 |
| 2006/0079906 A1* | 4/2006 | Timperley | A61B 17/1666 606/81 |

OTHER PUBLICATIONS

"Trabecular Metal Modular Acetabular System, Surgical Technique", Zimmer, Inc., 97-7255-029-00 Rev. 4, (May 2011), 16 pgs.

* cited by examiner

*Primary Examiner* — Andrew Yang
(74) *Attorney, Agent, or Firm* — Schwegman Lundberg & Woessner, P.A.

(57) ABSTRACT

Surgical systems and tools are disclosed including a surgical tool that has a shroud and a drive mechanism. The drive mechanism can have a distal end configured to connect to a surgical cutting instrument. The shroud can be configured to be disposed adjacent the distal end of the drive mechanism and can be adapted to be disposed between the drive mechanism and tissue of a patient.

20 Claims, 7 Drawing Sheets

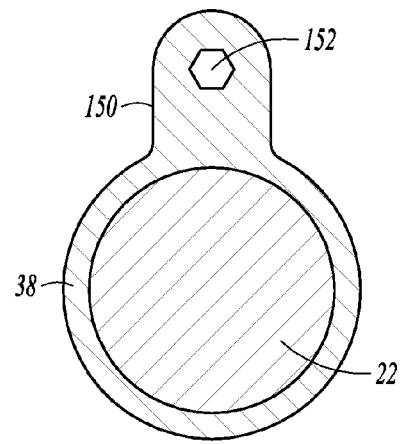
FIG. 3A
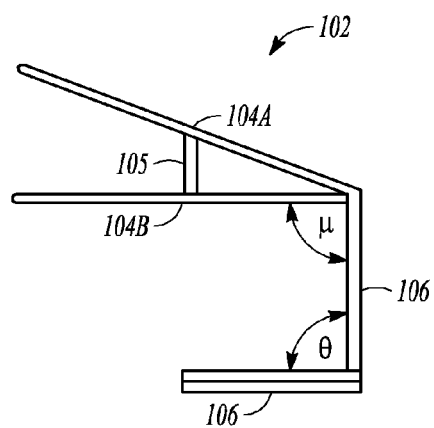   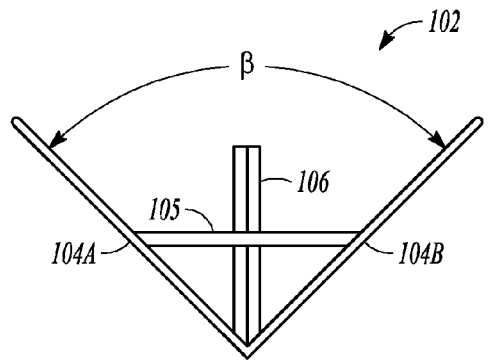
FIG. 4A                FIG. 4B

SURGICAL TOOL WITH SHROUD AND ALIGNMENT FEATURE

CLAIM OF PRIORITY

This application claims the benefit of U.S. Provisional Patent Application Ser. No. 62/082,249 filed on Nov. 20, 2014, the benefit of priority of which is claimed hereby, and which is incorporated by reference herein in its entirety.

TECHNICAL FIELD

The present patent application relates to hip arthroplasty, and more particularly, to surgical instruments for use in hip arthroplasty.

BACKGROUND

Orthopedic procedures may be used for the replacement of all, or a portion of, a patient's joint. Implantable prosthetic devices such as artificial hips, knees, ankles, elbows, and shoulders, can be inserted in the patient as part of these orthopedic procedures. Implantable devices should provide for ease of movement for the patient and should be appropriately sized, shaped and positioned to address applicable operational forces without failing or resulting in excessive patient discomfort. As part of a minimally invasive hip arthroplasty that can implant an artificial hip device in the acetabulum, surgical implements such as reamers have been developed to remove bone and tissue from the acetabulum to create an opening of a desired size and shape to receive an appropriately sized and shaped acetabular orthopedic implant therein.

OVERVIEW

The present inventor has recognized that drive mechanisms (e.g., shafts and associated linkages) used for rotary surgical instruments such as acetabular reamers can snag or otherwise come into contact with a patient's soft tissue during a hip arthroplasty. This can lead to patient discomfort, and can slow surgical operating time in some cases. Additionally, the inventor has recognized that proper surgical instrument alignment relative to the target anatomy (e.g., the acetabulum) can be difficult and/or time consuming to achieve. If alignment is incorrect implant placement can be impacted, which can lead to a non-ideal transfer of operational forces. This can necessitate further procedures. In view of the forgoing, the present application discloses a surgical tool that can include a shroud. In some examples, the surgical tool can include a drive shaft that has a distal end configured to connect to a surgical cutting instrument. The shroud can be configured to be disposed adjacent the distal end of the drive shaft and can be adapted to be disposed between the drive shaft and tissue of a patient. Thus, the shroud can be configured to protect the soft tissue of the patient from rotating components (e.g., the drive shaft) while reaming is performed. In further examples, the surgical tool can include an alignment feature configured to be disposed proximal of the shroud adjacent the drive shaft. In some cases the surgical tool can be used as part of a system that includes an alignment guide, which can be configured to couple to the alignment feature and can be adapted to allow for determination of an angle of the surgical cutting instrument relative to a target anatomy. Thus, the alignment guide can facilitate timely and proper surgical tool alignment relative to the target anatomy.

To better illustrate the devices disclosed herein, a non-limiting list of examples is provided here:

In Example 1, a surgical tool can comprise a drive mechanism having a distal end configured to connect to a surgical cutting instrument, and a shroud configured to be disposed adjacent the distal end and adapted to be disposed between the drive mechanism and tissue of a patient.

In Example 2, the tool of Example 1 wherein the surgical cutting instrument can comprise a reamer configured to remove a portion of an acetabulum.

In Example 3, the tool of any one or any combination of Examples 1 to 2, wherein the shroud can be adapted to form an opening that extends along a longitudinal length of the shroud from a distal end of the shroud to substantially a proximal end of the shroud, wherein the opening can allow for visibility of or access to the surgical cutting instrument.

In Example 4, the tool of any one or any combination of Examples 1 to 3, wherein the shroud can be configured to extend in substantially a 180° arc between the drive shaft and the tissue of the patient.

In Example 5, the tool of any one or any combination of Examples 1 to 4, can further comprise a sleeve adapted to receive at least a portion of the drive mechanism therein, and wherein the shroud can be configured to be attachable to and removable from the sleeve.

In Example 6, the tool of any one or any combination of Examples 1 to 4, can further comprise a sleeve adapted to receive at least a portion of the drive mechanism therein, and wherein the shroud is integral with and extends from a portion of the sleeve.

In Example 7, the tool of any one or any combination of Examples 1 to 4, can further comprise a sleeve adapted to receive at least a portion of the drive mechanism therein; and an alignment feature extending from the sleeve and projecting at an angle relative to an axis of rotation of the drive mechanism.

In Example 8, the tool of any one or any combination of Examples 1 to 4, can further comprise an alignment feature configured to be disposed proximal of the shroud adjacent the drive mechanism.

In Example 9, the tool of any one or any combination of Examples 7 to 8 can be used in combination with an alignment guide configured to couple to the alignment feature and adapted to allow for determination of an angle of the surgical cutting instrument relative to a target anatomy.

In Example 10, the tool of any one or any combination of Examples 7 to 9, wherein the alignment feature can comprise a projection that extends at an angle relative to an axis of rotation of the drive mechanism, and wherein the alignment feature forms an aperture adapted to receive a base member of the alignment guide.

In Example 11, the tool of any one or any combination of Examples 1 to 10 wherein the shroud can have at least one of a longitudinal length of between about 40 mm and about 80 mm, a proximal diameter of between about 5 mm and about 25 mm, and a flare angle of between 5° and 20°.

In Example 12, a shroud for a surgical tool, the shroud can comprise an attachment portion adapted to attach to a sleeve of the surgical tool and a body coupled to the attachment portion and adapted to surround a portion of a drive mechanism of the surgical tool. The body can be configured to form an opening that allows for visibility of or access to a surgical cutting instrument driven by the surgical tool.

In Example 13, the shroud of Example 12, wherein the opening can extend along a longitudinal length of the body from a distal end to a proximal end thereof.

In Example 14, the shroud of any one or any combination of Examples 12 to 13, wherein the body can have a first lip extending generally radially outward from a first edge of the shroud that defines the opening, and wherein the body has a second lip extending generally radially outward from a second edge of the shroud that defines the opening.

In Example 15, the shroud of any one or any combination of Examples 12 to 14, wherein the body can extend in substantially a 180° arc between the first edge and the second edge.

In Example 16, the shroud of any of Examples 12 to 15, wherein the body can be flared along the longitudinal length such that a diameter at the distal end thereof is larger than a diameter at a proximal end thereof.

In Example 17, the shroud of any one or any combination of Examples 12 to 15, wherein the attachment portion can have a longitudinal length of between about 5 mm and about 30 mm and a diameter of between about 5 mm and about 25 mm, and wherein the body has a longitudinal length of between about 20 mm to about 60 mm.

In Example 18, a surgical system that can comprise an alignment guide and a surgical tool configured to facilitate acetabular reaming of a patient. The surgical tool can comprise a drive shaft having a distal end configured to connect to a surgical reamer, a sleeve adapted to receive at least a portion of the drive mechanism therein and having an alignment feature adapted to couple to the alignment guide; and a shroud configured to be disposed adjacent the distal end and adapted to be disposed between the drive shaft and tissue of a patient.

In Example 19, the system of Example 18, wherein the alignment feature can project at an angle relative to an axis of rotation of the drive shaft, and wherein the alignment guide is adapted to allow for determination of an angle of the surgical cutting instrument relative to a target anatomy.

In Example 20, the system of any one or any combination of Examples 18 to 19, wherein the alignment feature can comprise a projection that extends at an angle relative to an axis of rotation of the drive shaft, and wherein the alignment feature forms an aperture adapted to receive a base member of the alignment guide.

In Example 21, the apparatus or system of any one or any combination of Examples 1-20 can optionally be configured such that all elements or options recited are available to use or select from.

These and other examples and features of the present devices and systems will be set forth in part in the following Detailed Description. This overview is intended to provide a summary of subject matter of the present patent application. It is not intended to provide an exclusive or exhaustive recitation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3A is a cross-sectional view through the surgical tool of FIG. 3.

FIG. 4A is a side perspective view of the alignment guide of FIG. 3.

FIG. 4B is a top plan view of the alignment guide of FIG. 4A.

DETAILED DESCRIPTION

The present application relates to surgical instruments and related systems, and in one example, to a surgical tool with a shroud for protecting the tissue of a patient during a surgical procedure. In an example, the surgical tool can include a drive mechanism that has a distal end configured to connect to a surgical cutting instrument. The shroud can be configured to be disposed adjacent the distal end of the drive mechanism and can be adapted to be disposed between the drive mechanism and the tissue of the patient. Thus, the shroud can be configured to protect the tissue of the patient from rotating components (e.g., the drive mechanism). In other examples, the surgical tool can be used as part of a system that can include various features that can facilitate timely and proper surgical alignment of the surgical tool relative to a target anatomy.

Figure 1:
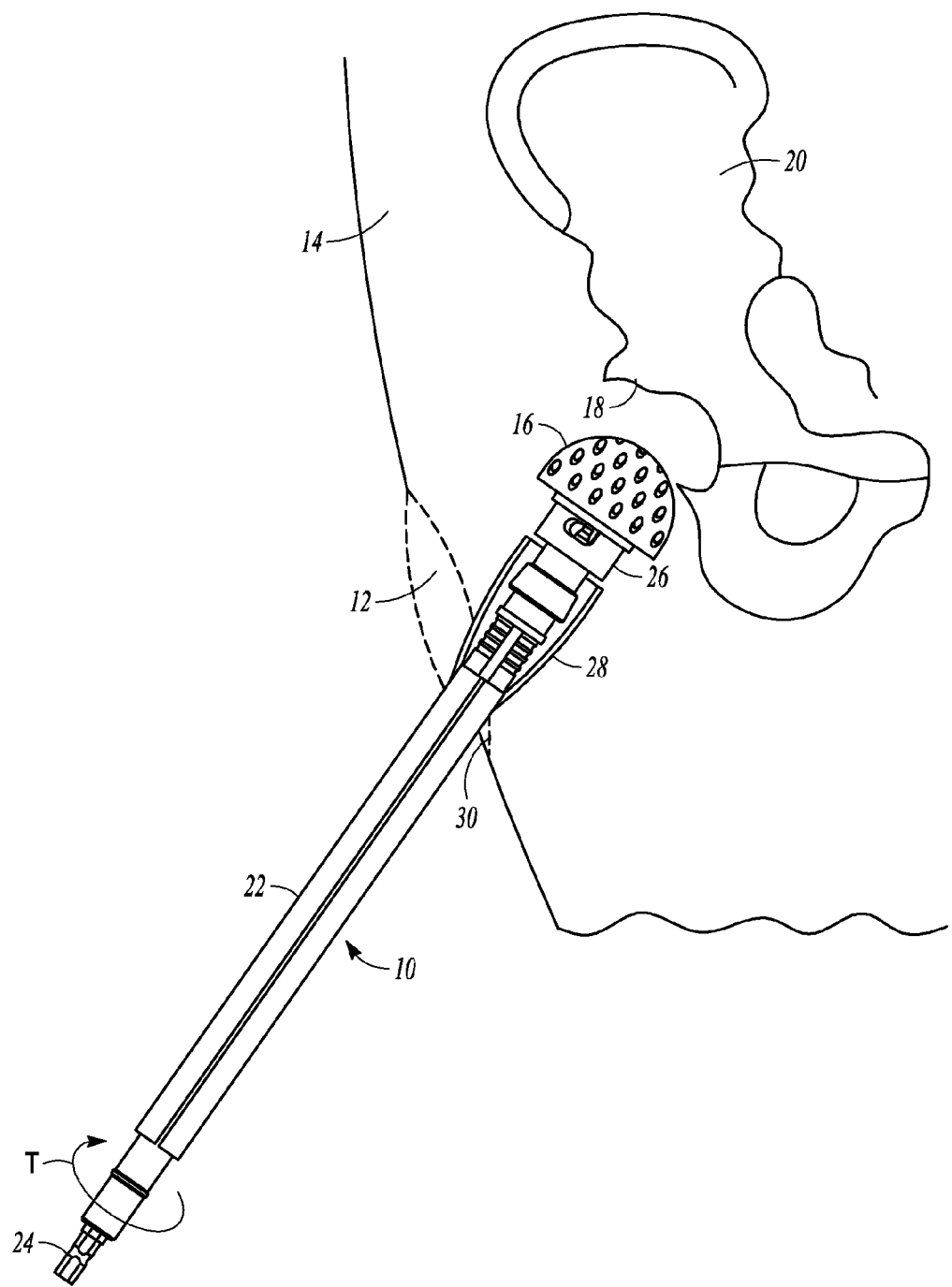
FIG. 1 is a plan view showing a surgical tool including a drive shaft, a single piece shroud and sleeve and a reamer being used in a minimally invasive surgical procedure to ream the acetabular socket of a hip according to an example of the present disclosure.

FIG. 1 shows a surgical tool 10 passing through an incision 12 in tissue 14 of a patient. The surgical tool 10 can include a reamer 16 that can ream an acetabular socket 18 of an acetabulum 20. In FIG. 1, the surgical tool 10 is shown disposed adjacent the acetabulum 20 and oriented to ream the acetabular socket 18.

As shown in FIG. 1, the surgical tool 10 can include a drive shaft 22 adapted to be coupled to the reamer 16. The drive shaft 22 can include a proximal end 24 and a distal end 26. The proximal end 24 can be configured to couple to a drive or another linkage for torque transmission (as indicated by arrow T) to the drive shaft 22 and ultimately to the reamer 16. Similarly, the distal end 26 of the drive shaft 22 can be configured to connect to a rotary surgical cutting instrument (e.g., the reamer 16). Although illustrated in reference to a single shaft, the drive shaft 22 can include other known torque transfer mechanisms in other examples (e.g., gears, a series of interconnected shafts, etc.).

As illustrated in FIG. 1, a shroud 28 can be configured to be disposed adjacent the distal end 26 and can be adapted to be disposed between the drive shaft 22 and the tissue 14 of the patient such as along an edge 30 of the incision 12. In some cases, the shroud 28 can be configured to extend in substantially a 180° arc between the drive shaft 22 and the tissue 14 (e.g., along edge 30) of the patient. As will be discussed subsequently, the shroud 28 can be coupled to a stationary sleeve that forms a handle of the surgical tool 10. Thus, the shroud 28 can be fixed relative to the drive shaft 22. Because the shroud 28 can be at least partially disposed between the rotating drive shaft 22 and the tissue 14, the shroud 28 can reduce trauma to the tissue 14 that can result from rotation of the drive shaft 22.

Figure 2:
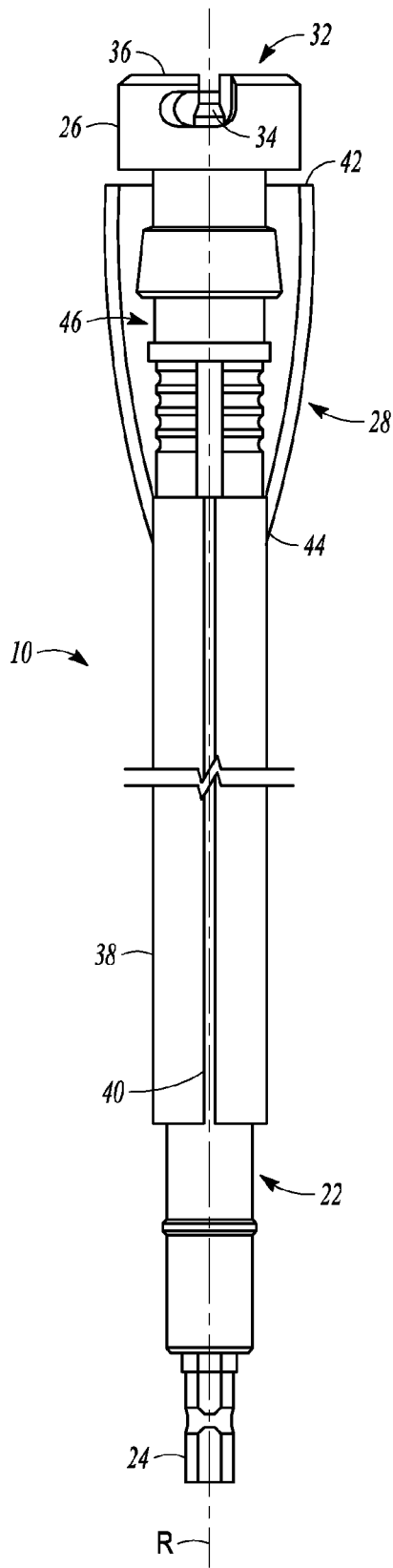
FIG. 2 is a plan view of the tool of FIG. 1 with the reamer removed.

FIG. 2 shows a plan view of the surgical tool 10 including the drive shaft 22 according to an example. FIG. 2 illustrates the proximal end 24 of the drive shaft 22 can comprise a fitting or similar coupling mechanism, which is adapted to be joined to a torque source or torque transferring linkage that can be coupled to a torque source. Thus, the drive shaft 22 can have an axis of rotation R as illustrated in FIG. 2. The distal end 26 can be configured as a retention feature to selectively couple with the surgical cutting instrument (e.g., the reamer 16 of FIG. 1). The configuration of the retention feature can be selected from a variety of mechanisms for receiving and retaining the surgical cutting instrument. Many such retention mechanisms exist, however a bayonet style mechanism 32 is shown for exemplary purposes. The bayonet style mechanism 32 can comprise a pin carrying component 34. The pin carrying component 34 works cooperatively with a catch 36 located at the distal end 26 to form the bayonet for capturing different size surgical cutting instruments (e.g. different sized reamers).

As shown in FIG. 2, a sleeve 38 can be disposed about a portion of the drive shaft 22 in some instances. Thus, the sleeve 38 can be adapted to receive at least a portion of the drive shaft 22 therein. The sleeve 38 can be designed with a split-line 40 that can facilitate the disposition of the sleeve 38 around and/or the removal of the sleeve 38 from around the drive shaft 22. As discussed, the sleeve 38 can be adapted to be substantially stationary relative to the drive shaft 22. Thus, the sleeve 38 can comprise a housing for the drive shaft 22 and can be used as a handle for the tool. Although not shown in the discussed examples, a plurality of sleeves can be layered or otherwise disposed around one another. The shroud 28 can be coupled to one or more of these sleeves and can extend generally longitudinally in a distal direction relative thereto toward the distal end 26 of the drive shaft 22. In some cases the shroud 28 can extend from a more proximal portion of the sleeve 38. In some examples, the shroud 28 can be integral with the sleeve 38. Thus, the shroud 28 can be formed from a same material as the sleeve 38 (e.g., surgically certified plastic, etc.) and can be extruded or otherwise formed along with the sleeve 38, in some cases. As will be discussed subsequently with regard to the examples of FIGS. 5A-5C, the shroud can also comprise a separate component that can be configured to be attachable to and removable from the sleeve 38.

According to one example, the sleeve 38 can extend longitudinally along a length of the drive shaft 22 that can comprise between about 150 mm and about 250 mm. Similarly, the shroud 28 can have a longitudinal length of between about 40 mm and about 80 mm. In some cases, the longitudinal length of the shroud 28 can be about 60 mm. A proximal diameter of shroud 28 and the sleeve 38 can be between about 5 mm and about 25 mm. In some instances, the diameter can be between about 15 mm and about 20 mm. As illustrated in the example of FIG. 2, the shroud 28 can have a flare angle of between 5° and 20°. Thus, in some examples, the shroud 28 can be flared along its longitudinal length such that a diameter at the distal end 42 of the shroud 28 is larger than a diameter at a proximal end 44 of the shroud 28.

The shroud 28 can have openings at both the distal end 42 and the proximal end 44. The proximal end 44 opening can be formed or otherwise coupled to the sleeve 38 about the drive shaft 22. The distal end 42 opening can be spaced about at least a portion of the distal end 26 of the drive shaft 22 adjacent the surgical cutting instrument (e.g., the reamer 16 of FIG. 1). In some instances, the shroud 28 is disposed around only a portion of the drive shaft 22 comprising an area likely to come into contact with a patient's tissue. Thus, the shroud 28 can be adapted to form an opening 46 that extends along a longitudinal length of the shroud 28 from the distal end 42 of the shroud to substantially the proximal end 44 of the shroud 28. This opening 46 can be in an area that has a low likelihood of the drive shaft 22 coming into contact with the tissue of the patient. In some instances, the opening allows for visibility of or access to the surgical cutting instrument (e.g., the reamer 16 of FIG. 1).

Figure 3:
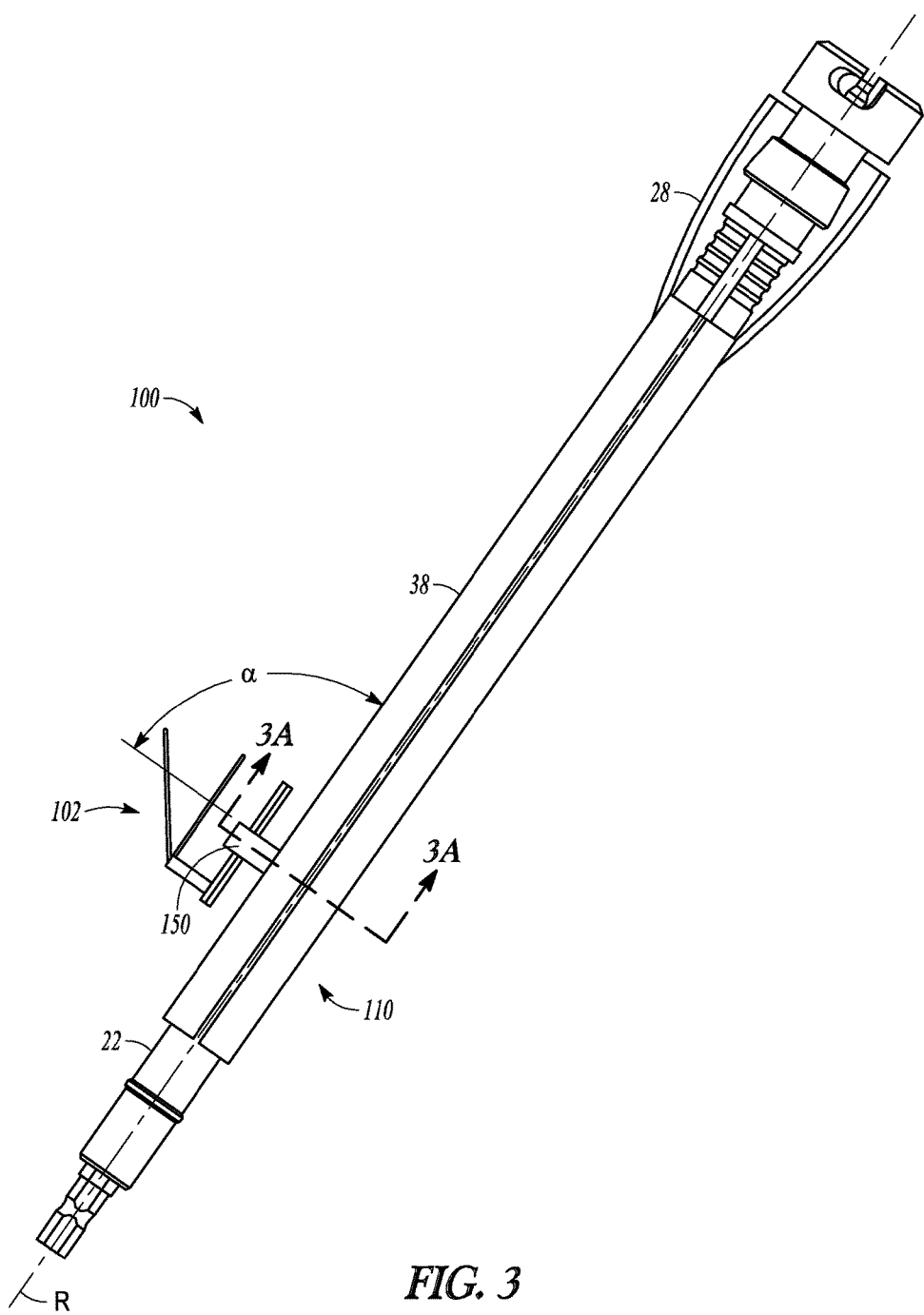
FIG. 3 is a plan view of a surgical tool with an alignment guide according to an example of the present disclosure.

FIG. 3 illustrates a surgical tool 110 according to another example as part of a system 100 that includes an alignment guide 102. As shown in FIG. 3, the alignment guide 102 can be mounted to the surgical tool 110 and is adapted to be gripped by a hand of a surgeon. The surgical tool 110 can include some of the same or similar features and components (e.g. drive shaft 22, shroud 28, sleeve 38, etc.) previously discussed with regard to the surgical tool 10 of FIGS. 1-2. Thus, these features and components will not be discussed in great detail with regard to the surgical tool 110 of FIG. 3. The surgical tool 110 can include an alignment feature 150. The alignment feature 150 can be configured to be disposed proximal of the shroud 28 adjacent the drive shaft 22. More particularly, the alignment feature 150 can be coupled to the sleeve 38 and can extend therefrom. In some instances, the alignment feature 150 can be integrally formed (e.g. extruded, etc.) along with the sleeve 38.

As illustrated in FIG. 3, the alignment feature 150 can project from the sleeve 38 at an angle α relative to an axis of rotation R of the drive shaft 22. The alignment feature 150 can be disposed along the sleeve 38 about 80 mm to 200 mm from a distal end thereof. According to one example, the alignment feature 150 can extend about 20 mm to 40 mm outward of a diametrical surface of the sleeve 38. In further examples, the alignment feature 150 can have a thickness in the longitudinal direction of about 5 mm to 20 mm.

FIG. 3A shows a cross-section through the alignment feature 150, the sleeve 38, and the shaft 22 of FIG. 3. The alignment guide 102 is not shown in FIG. 3A. FIG. 3A illustrates that the alignment feature 150 can comprise a flange shaped projection from the sleeve 38 and can form an aperture 152 adapted to receive a portion (e.g., a base member) of the alignment guide 102 (FIG. 3) therein. In some cases the aperture 152 can be hexagonally or otherwise shaped to match the shape of the alignment guide 102. Such a shape can restrict rotational movement of the alignment guide 102 relative to the alignment feature 150 when the alignment guide 102 is inserted therein. As shown in FIG. 3, the alignment feature 150 can rise at angle α relative to the single piece sleeve 38.

FIGS. 4A and 4B provide further illustration of the alignment guide 102 from various perspectives. The alignment guide 102 can be used during hip arthroplasty to assist the surgeon in positioning the reamer coupled to the distal end of the surgical tool 110 (FIG. 3) at a proper angle with respect to the acetabulum of the patient. This angle can allow for an implant placement that will transfer operational forces desirably (e.g., to the femoral head). Thus, the alignment guide can facilitate timely and proper surgical tool alignment relative to the acetabulum of the patient.

The alignment guide 102 can include first and second members 104A and 104B that are joined to a body 106 (FIG. 4A). The first and second members 104A and 104B can be disposed at an angle β (FIG. 4B) from one another. In some cases, the angle β can be substantially 90°. A cross-member 105 (FIG. 4B) can be coupled to both the first and second members 104A and 104B and spaced from the body 106. Both the first and second members 104A and 104B can be disposed at an angle μ (FIG. 4A) relative to the body 106. In some cases, the angle μ can be substantially 90°. A base member 108 can extend from the body 106 at an angle θ. In some examples, the angle θ can be substantially 90°. In some instances, the base member 108 can have a cross-sectional configuration (e.g. a hexagonal cross-section) that is adapted to be received in the aperture 152 (FIG. 3B).

Together the first and second members 104A and 104B and cross-member 105 form an A shape that provides a means for the surgeon to visually check the alignment of the surgical tool (in particular the reamer) with anatomical check points on the patient and/or with features in the surgical area (e.g., the floor). For example, the body 106 can attach to the alignment feature 150 (FIGS. 3A and 3B) to produce a desired angle which allows the alignment guide 102 and both the first and second members 104A and 104B to arranged such that one member (104A or 104B) can be substantially parallel with a sagittal plane of the patient and the second member (104A or 104B) can be substantially aligned with the long axis of the body 106. In use, the surgeon can orient the surgical tool with the reamer relative to the acetabulum until a desired angle is achieved as verified by the alignment guide 102. Actuation of the drive shaft to cause rotation of the reamer to remove portions of the acetabulum can then occur.

Figure 5A:
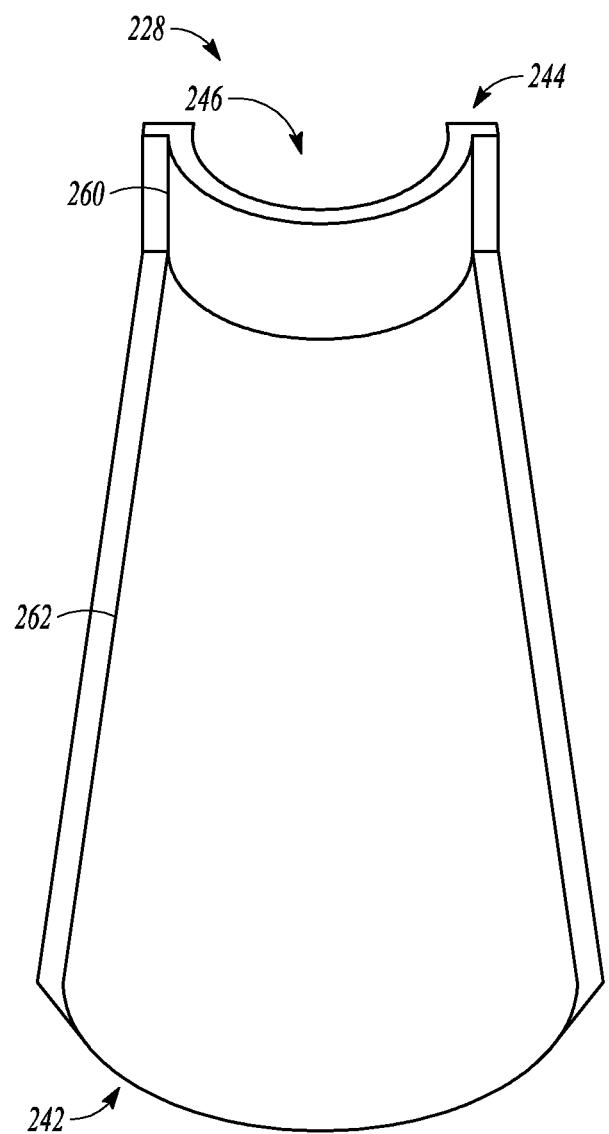
FIG. 5A is perspective view of an attachable and detachable shroud from a first side according to an example of the present disclosure.
Figure 5B:
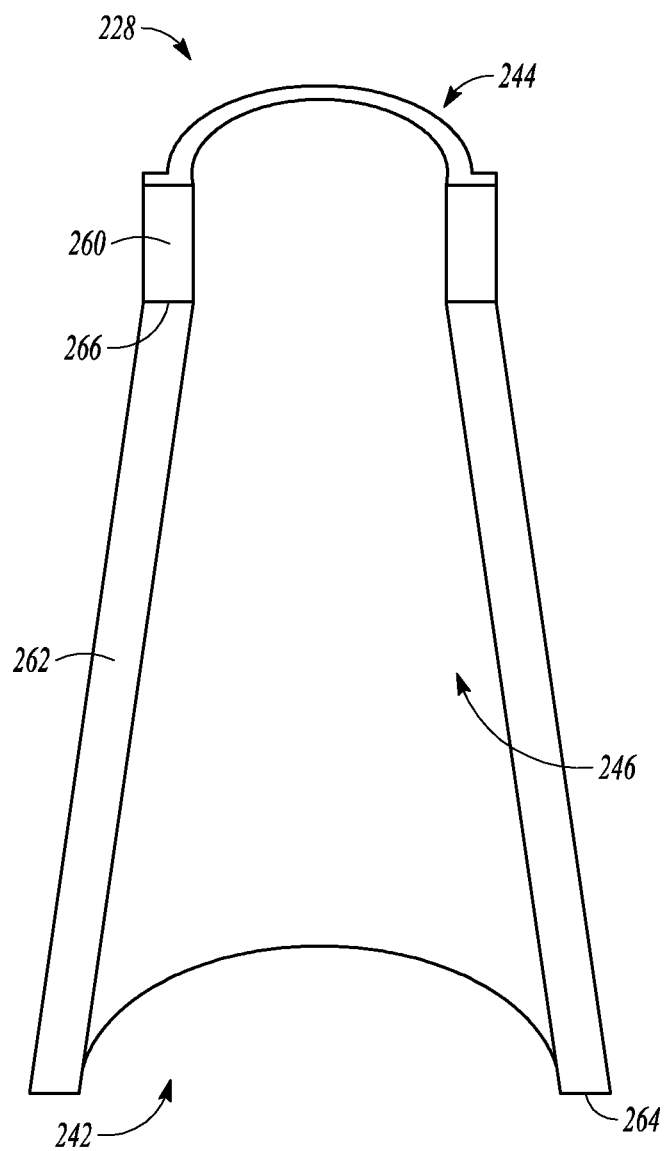
FIG. 5B is a perspective view of the shroud of FIG. 5A as viewed from a second side.
Figure 5C:
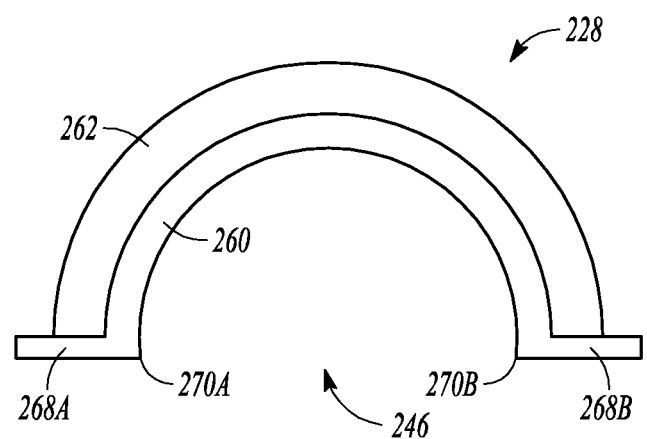
FIG. 5C is a plan view of a proximal end of the shroud of FIGS. 5A and 5B.

FIGS. 5A-5C illustrate a shroud 228 that can be used as an attachable and detachable feature with a surgical tool such as surgical tools 10 and 110 (FIGS. 1-3) instead of the integral shroud and sleeve design (e.g., previously disclosed shroud 28). The shroud 228 can be a separately constructed device that can be configured to be attachable to and removable from the sleeve 22 (FIGS. 1-3). Thus, the shroud 228 can be clipped, snapped, or otherwise attached to the sleeve 22 (FIGS. 1-3) prior to the surgical procedure and can be removed and disposed of after the surgery.

FIG. 5A shows a perspective view of a first side of the shroud 228. FIG. 5B shows a perspective view of a second side of the shroud 228. FIG. 5C illustrates a proximal end 244 of the shroud 228. The shroud 228 can include a distal end 242, an opening 246, an attachment portion 260, and a body 262. As discussed, both the distal end 242 and the proximal end 244 can include openings adapted to allow passage of the drive shaft. Similarly, the body 262 and/or the attachment portion 260 can be configured to form the opening 246 that allows for visibility of or access to a surgical cutting instrument driven by the surgical tool.

The attachment portion 260 can have a semicircular cross-section in some examples and can be adapted to attach to the sleeve 22 (FIGS. 1-3). The body 262 can be coupled to the attachment portion 260 and can be adapted to surround a portion of the drive shaft 22 (FIGS. 1-3). The body 262 can be integrally formed (e.g., extruded, etc.) with the attachment portion 260. The body 262 can be flared along its longitudinal length such that a diameter at the distal end 264 is larger than a diameter at a proximal end 266.

In some cases, the body 262 can have a semicircular cross-section similar to the attachment portion 260 with an interior accessible by opening 246. The attachment portion 260 can have a longitudinal length of between about 5 mm and about 30 mm and can have a diameter of between about 5 mm and about 25 mm, according to one example. In some cases, the body 262 can have a longitudinal length of between about 20 mm to about 60 mm. The opening 246 can extend along the longitudinal length of the body 262 from the distal end 264 to the proximal end 266. In some instances, the opening 246 can also be formed by the attachment portion 260.

As illustrated in the example of FIG. 5C, the body 262 can have a first lip 268A that can extend generally radially outward from a first edge 270A of the shroud 228 that defines the opening 246. The body 262 has a second lip 268B that can extend generally radially outward from a second edge 270B of the shroud 228 that defines the opening 246. In some instances, the attachment portion 260 can include the first lip and the second lip as well. The body 262 can extend in substantially a 180° arc between the first edge 270A and the second edge 270B.

Although specific configurations of the surgical tool for acetabular reaming including the shroud and other components are shown in FIGS. 1-5C and particularly described above, other designs of surgical devices that fall within the scope of the claims are anticipated. For example, the shroud described herein can be used, for example, in various orthopedic procedures including procedures on knees and shoulders. Indeed, surgical reamers for knee and shoulder procedures could benefit from the shroud as illustrated and described herein.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed:

1. A surgical tool comprising:
    a surgical cutting instrument;
    a drive mechanism having a distal end configured to connect to the surgical cutting instrument; and
    a shroud coupled to the drive mechanism and having a fixed position relative to a longitudinal length of the drive mechanism when coupled thereto, wherein during operable use of the surgical tool to remove a part of a bone of a patient, the shroud is positioned along the longitudinal length such that that shroud is spaced proximal of the distal end of the drive mechanism and spaced proximal of the surgical cutting instrument such that the surgical cutting instrument and the distal end are unobstructed by the shroud so as to be fully exposed to allow the surgical cutting instrument to remove the part of the bone, wherein the shroud is configured to surround a portion of the drive mechanism and be disposed between the drive mechanism and a soft tissue of the patient to block the soft tissue from engaging the drive mechanism during operable use of the surgical tool to remove the part of the bone.

2. The tool of claim 1 wherein the surgical cutting instrument comprises a reamer configured to remove a portion of an acetabulum.

3. The tool of claim 1, wherein the shroud is adapted to form an opening that extends along a longitudinal length of the shroud from a distal end of the shroud to substantially a proximal end of the shroud, wherein the opening allows for visibility of or access to the surgical cutting instrument.

4. The tool of claim 1, wherein the shroud is configured to extend in substantially a 180° arc between the drive shaft and the tissue of the patient.

5. The tool of claim 1, further comprising a sleeve adapted to receive at least a portion of the drive mechanism therein, and wherein the shroud is configured to be attachable to and removable from the sleeve.

6. The tool of claim 1, further comprising a sleeve adapted to receive at least a portion of the drive mechanism therein, and wherein the shroud is integral with and extends from a portion of the sleeve.

7. The tool of claim 1, further comprising:
    a sleeve adapted to receive at least a portion of the drive mechanism therein; and
    an alignment feature extending from the sleeve and projecting at an angle relative to an axis of rotation of the drive mechanism.

8. The tool of claim 1, further comprising an alignment feature configured to be disposed proximal of the shroud adjacent the drive mechanism.

9. The tool of claim 8, in combination with an alignment guide configured to couple to the alignment feature and adapted to allow for determination of an angle of the surgical cutting instrument relative to a target anatomy.

10. The tool of claim 9, wherein the alignment feature comprises a projection that extends at an angle relative to an axis of rotation of the drive mechanism, and wherein the alignment feature forms an aperture adapted to receive a base member of the alignment guide.

11. The tool of claim 1, wherein the shroud has at least one of a longitudinal length of between about 40 mm and about 80 mm, a proximal diameter of between about 5 mm and about 25 mm, and a flare angle of between 5° and 20°.

12. A shroud for a surgical tool, the shroud comprising:
    an attachment portion adapted to attach to a sleeve of the surgical tool, wherein when attached to the sleeve, the shroud has a fixed position relative to a longitudinal length of the drive mechanism; and
    a body coupled to the attachment portion and adapted to surround a portion of the drive mechanism of the surgical tool distal of a connection between the drive mechanism and a surgical cutting instrument such that the surgical cutting instrument is unobstructed by the body during operable use of the surgical tool to remove a part of a bone of a patient;
    wherein the body is configured to form an opening that allows for visibility of or access to the surgical cutting instrument driven by the surgical tool, and wherein the body is configured to surround a portion of the drive mechanism and be disposed between the drive mechanism and a soft tissue of the patient to block the soft tissue from engaging the drive mechanism.

13. The shroud of claim 12 wherein the opening extends along a longitudinal length of the body from a distal end to a proximal end thereof.

14. The shroud of claim 12, wherein the body has a first lip extending generally radially outward from a first edge of the shroud that defines the opening, and wherein the body has a second lip extending generally radially outward from a second edge of the shroud that defines the opening.

15. The shroud of claim 12, wherein the body extends in substantially a 180° arc between the first edge and the second edge.

16. The shroud of claim 12, wherein the body is flared along the longitudinal length such that a diameter at the distal end thereof is larger than a diameter at a proximal end thereof.

17. The shroud of claim 12, wherein the attachment portion has a longitudinal length of between about 5 mm and about 30 mm and a diameter of between about 5 mm and about 25 mm, and wherein the body has a longitudinal length of between about 20 mm to about 60 mm.

18. A surgical system comprising:
    an alignment guide; and
    a surgical tool configured to facilitate acetabular reaming of a patient, the surgical tool comprising:
        a surgical reamer;
        a drive shaft having a distal end configured to connect to the surgical reamer;
        a sleeve adapted to receive at least a portion of the drive shaft therein and having an alignment feature adapted to couple to the alignment guide; and
        a shroud configured to couple with the sleeve and having a fixed position relative to a longitudinal length of the drive shaft when the sleeve receives the drive shaft and the shroud is coupled to the sleeve, wherein during operable use of the surgical tool to remove a part of a bone of a patient, the shroud is positioned along the longitudinal length such that that shroud is spaced proximal of the distal end of the drive shaft and spaced proximal of the surgical reamer such that the surgical reamer and the distal end are unobstructed by the shroud so as to be fully exposed to allow the reamer to remove the part of the bone, wherein the shroud is configured to surround a portion of the drive shaft and be disposed between the drive shaft and a soft tissue of the patient to block the soft tissue from engaging the drive shaft.

19. The system of claim 18, wherein the alignment feature projects at an angle relative to an axis of rotation of the drive shaft, and wherein the alignment guide is adapted to allow for determination of an angle of the surgical reamer relative to a target anatomy.

20. The system of claim 18, wherein the alignment feature comprises a projection that extends at an angle relative to an axis of rotation of the drive shaft, and wherein the alignment feature forms an aperture adapted to receive a base member of the alignment guide.

* * * * *

UNITED STATES PATENT AND TRADEMARK OFFICE
CERTIFICATE OF CORRECTION

PATENT NO. : 10,022,133 B2
APPLICATION NO. : 14/868697
DATED : July 17, 2018
INVENTOR(S) : John J. Hudak, Jr.

Page 1 of 1

It is certified that error appears in the above-identified patent and that said Letters Patent is hereby corrected as shown below:

In the Claims

In Column 9, Line 26, in Claim 1, delete "that" and insert --the-- therefor

In Column 10, Line 67, in Claim 18, delete "that" and insert --the-- therefor

Signed and Sealed this
Fourth Day of June, 2019

Andrei Iancu
*Director of the United States Patent and Trademark Office*